United States Patent
Polig et al.

(10) Patent No.: US 11,521,705 B2
(45) Date of Patent: Dec. 6, 2022

(54) RANDOM SEQUENCE GENERATION FOR GENE SIMULATIONS

(71) Applicant: International Business Machines Corporation, Armonk, NY (US)

(72) Inventors: Raphael Polig, Langnau am Albis (CH); Mitra Purandare, Zurich (CH)

(73) Assignee: International Business Machines Corporation, Armonk, NY (US)

( * ) Notice: Subject to any disclaimer, the term of this patent is extended or adjusted under 35 U.S.C. 154(b) by 1115 days.

(21) Appl. No.: 16/134,222

(22) Filed: Sep. 18, 2018

(65) Prior Publication Data

US 2020/0089842 A1 Mar. 19, 2020

(51) Int. Cl.
*G16B 5/00* (2019.01)
*G16B 30/00* (2019.01)
*G06F 30/00* (2020.01)
*G06G 7/48* (2006.01)

(52) U.S. Cl.
CPC ............ *G16B 5/00* (2019.02); *G06F 30/00* (2020.01); *G16B 30/00* (2019.02); *G06G 7/48* (2013.01)

(58) Field of Classification Search
CPC .. G16B 5/00; G16B 30/00; G16B 5/10; G06F 30/00; G06F 9/451; G06F 13/16; G06F 21/86; G06G 7/48; H04L 9/32; H04L 63/061; H04N 19/136
See application file for complete search history.

(56) References Cited

U.S. PATENT DOCUMENTS

| | | | | |
|---|---|---|---|---|
| 9,542,641 | B2 | 1/2017 | Abdi et al. | |
| 9,667,979 | B2 * | 5/2017 | Iizuka | H04N 19/136 |
| 2011/0277021 | A1 * | 11/2011 | Ogawa | G06F 21/36 |
| | | | | 726/6 |
| 2013/0282352 | A1 | 10/2013 | Gray et al. | |
| 2016/0283626 | A1 | 9/2016 | Yu | |
| 2017/0034167 | A1 * | 2/2017 | Figueira | H04L 63/061 |
| 2018/0076957 | A1 * | 3/2018 | Watanabe | G06F 21/602 |

FOREIGN PATENT DOCUMENTS

| | | | | |
|---|---|---|---|---|
| CN | 1675876 A | * | 9/2005 | G06F 21/86 |
| CN | 103019831 A | * | 4/2013 | G06F 9/451 |
| CN | 103309825 B | * | 4/2017 | G06F 13/16 |
| JP | 2005292412 A | * | 10/2005 | |
| JP | 2012135005 A | * | 7/2012 | H04L 9/32 |
| JP | 2014236961 A | * | 12/2014 | |

OTHER PUBLICATIONS

Figueira et al., U.S. 2017/0034167 A1, Feb. 2017, see the shortened version.*

(Continued)

*Primary Examiner* — Kandasamy Thangavelu
(74) *Attorney, Agent, or Firm* — Scully, Scott, Murphy & Presser, P.C.; Daniel P. Morris (57) ABSTRACT

A random sequence generation of defined values may be provided. A method comprises pre-loading a RAM block with an initial list comprising the defined values of a sequence of values to be updated, and shuffling the defined values of the sequence using a counter and a random offset for indices in the list.

18 Claims, 7 Drawing Sheets

100 method 102 pre-loading a RAM Block with an initial list comprising defined values of a sequence to be updates 104 shuffling the defined values of the sequence using a counter and a random offset for indices in the list (56) References Cited

OTHER PUBLICATIONS

Iizuka et al., U.S. Pat. No. 9,667,979 B2, May 2017, see shortened version.*
Miskov-Zivanov, N., et al., "Emulation of Biological Networks in Reconfigurable Hardware", ACM-BCB '11 Proceedings of the 2nd ACM Conference on Bioinformatics, Computational Biology and Biomedicine, Aug. 1-3, 2011, pp. 536-540.
Miskov-Zivanov, N., et al., "Regulatory Network Analysis Acceleration with Reconfigurable Hardware," 2011 Annual International Conference of the IEEE Engineering in Medicine and Biology Society, Manuscript received Apr. 25, 2011, Aug. 2011, pp. 149-152.

* cited by examiner 100 method 102 pre-loading a RAM Block with an initial list comprising defined values of a sequence to be updates 104 shuffling the defined values of the sequence using a counter and a random offset for indices in the list

RANDOM SEQUENCE GENERATION FOR GENE SIMULATIONS

BACKGROUND

The present disclosure relates generally to a method for a random sequence generation of defined values, and more specifically, to random sequence generation of defined values for gene regulatory network simulations in hardware. The present disclosure relates further to a random sequence generator for defined values, and a computer program product.

Currently, a plurality of mechanisms of biological systems is simulated—in particular, regulatory dependencies in the human body. Cellular functions in any organism are fundamentally controlled by its genes. However, genes do not work in isolation, but rather function together with other genes in complex dependency networks. In order to understand more about cellular mechanisms, interactions between the genes ought to be studied. One of the popular qualitative modeling formalism for gene regulatory networks is a Boolean network.

An important facet that can be studied with Boolean models is the response of a gene network to a pattern of input stimuli. Running the model provides a simulation of how the network evolves over time. The ever-increasing size and complexity of Boolean models due to available gene measurement and inference techniques results in long simulation times. Asynchronous update schemes, aimed at a contact for this diversity, update only one randomly chosen gene at a time. This is computationally expensive. For generating the stimuli, fast random number generators with specific characteristics are required in order to not slow down the simulation by the random number generators.

Known technologies, like linear-feedback shift register for generating random numbers—or better pseudo-random numbers—cannot guarantee a list of unique values. However, this is required because in a synchronous Boolean network simulation, an update value must be generated, wherein each node is updated only once per time step. Also, ranked update orders require specific nodes to be updated earlier than others, requiring multiple random ranges.

SUMMARY

According to one aspect of the present invention, a method for a random sequence generation of defined values may be provided. The method may comprise pre-loading a RAM block with an initial list comprising the defined value of a sequence of values to be updated, and shuffling the defined values of the sequence using a counter and a random offset for indices in the list.

According to another aspect of the present invention, a random sequence generator for defined values may be provided. The random sequence generator may comprise RAM block comprising storage cells for storing an integer value each, wherein the integer values represent an initial list with the defined values of a sequence of values to be updated, and a shuffling unit adapted for shuffling the values of the sequence using a counter and a random offset for indices in the list.

It may be noted that the result of the counter together with the random offset may reside always within a defined index value range of the sequence.

Furthermore, embodiments may take the form of a related computer program product, accessible from a computer-usable or computer-readable medium providing program code for use, by, or in connection, with a computer or any instruction execution system. For the purpose of this description, a computer-usable or computer-readable medium may be any apparatus that may contain means for storing, communicating, propagating or transporting the program for use, by, or in connection, with the instruction execution system, apparatus, or device.

BRIEF DESCRIPTION OF THE DRAWINGS

It should be noted that embodiments of the invention are described with reference to different subject-matters. In particular, some embodiments are described with reference to method type claims, whereas other embodiments are described with reference to apparatus type claims. However, a person skilled in the art will gather from the above and the following description that, unless otherwise notified, in addition to any combination of features belonging to one type of subject-matter, also any combination between features relating to different subject-matters, in particular, between features of the method type claims, and features of the apparatus type claims, is considered as to be disclosed within this document.

The aspects defined above, and further aspects of the present invention, are apparent from the examples of embodiments to be described hereinafter and are explained with reference to the examples of embodiments, but to which the invention is not limited.

Embodiments of the invention will be described, by way of example only, and with reference to the following drawings.

DETAILED DESCRIPTION

In the context of this description, the following conventions, terms and/or expressions may be used:

The term 'random sequence generation' may here denote a process in which pseudo-random numbers are generated. However, in the context of this document the random number generation may have a constraint in that the random number may only be selected out of a predefined number pool.

The term 'defined values' may denote a group of integer values from which one of the numbers may be selected randomly. The defined values may be in a sequential order or may be selected by any other rule.

The term 'RAM block' may denote a group of memory cells, each adapted to store one of the defined values. The storage cells may be instrumented with a dual port option so that data values may be written via a write port and data may be read via the read port. This way, a fast read/write cycle may be available if compared to a single port storage cell.

The term 'shuffling' may denote an exchange of values in a group of storage cells like the RAM block so that the integer values stored in the cells have a different—in particular randomly order.

The term 'counter' may denote a number generator adapted for generating a consecutively growing number of output values. This may apply to an up-counter or increment counter. In contrast, there may also be a decrement counter. A decrement counter may start with a start number and may decrease the output value at every clock cycle by 1—or another predefined number.

The term 'random offset' may denote an integer value which may be generated randomly. In some cases in the context of this document, the random offset may have constraints in the sense that only a limited number of different random offset values may be allowable.

The term 'local cycle' may denote an exchange—or a mini-shuffling—of two values in the RAM block, i.e., an exchange of the values stored in two storage cells.

The term 'constraint modulo value generator' may denote a generator typically implemented in hardware. However, a software implementation may also be possible. The constraint modulo value generator may be designed in order to generate a random number or better an offset with only a limited group of allowable value. The constraint modulo value generator will be described in more detail below.

The proposed method for a random sequence generation of defined values may offer multiple advantages and technical effects:

Specific requirements for a random number generation to be used in gene regulatory networks using Boolean models are addressed. In particular, the pseudo-random numbers generated by the proposed device and related method may guarantee that only defined random numbers (generated members are not repeated accidentally) in a sequence of numbers are generated. Hence, the same index is not generated twice in a given sequence of defined numbers.

Additionally, by implementing the proposed random number generator in hardware, the generation of the limited and constrained set of random numbers is very fast. Thus, the simulation of gene regulatory networks is not be slowed down by random number generators, required to generate a plurality of stimuli for the gene regulatory network simulated by the Boolean models.

Thus, the implementation may be done using an FPGA (field programmable gate array) in an efficient and comparably cheap way. The generation of the constraint random number may elegantly be adapted to a varying number in a given sequence of numbers and thus the simulated stimuli. Consequently, multiple random ranges (e.g., for ranked update orders) can be addressed easily, so as to reflect dependencies in the simulating Boolean network reflecting dependencies of the gene regulatory networks and its stimuli. Therefore, it is fair to say that the available hardware resources for the simulation process are optimized in terms of hardware usage because of these hardware resources do not have to run in wait states waiting for the next randomly generated sequence of defined values.

The proposed method additionally allows operating three (or two or more) of the proposed random number generators in parallel—but time-shifted—in order to get a continuous stream of constraint random numbers, for the simulation of the gene regulatory networks.

According to one permissive embodiment of the method, the shuffling may exchange two defined values in each local cycle. In other words, a completely new sequence of defined values may be determined after a plurality of local cycles. This step-by-step approach allows a comparably simple algorithm which may be implementable in hardware without complex circuitry.

According to one embodiment of the method, a start value of the counter may be zero and an end value of the counter may be equal to a length value of the list minus 1. E.g., if the number of values is, e.g., 50, then, the length of value may be 49. Additionally, each counter increase may represent one local cycle. Thus, a controlled approach is taken to walk through the complete sequence of defined values—i.e., each index of the cells of the RAM block—without the danger to skip one of the cells in the RAM block.

According to another embodiment of the method, a global cycle of the shuffling may be completed after the counter may have run through all values from the start value to the end value resulting in a new sequence of the defined values. Thus, a new random sequence—e.g., stimuli for the gene regulatory network—of defined values may be generated in every global cycle.

According to one embodiment of the method, in each of the local cycles only those values of the sequence may be exchanged or shuffled that have not been shuffled in a previous local cycle. Hence, only the remaining values in the list are addressed by an index. Those cells in the RAM block that have been addressed by a local cycle before within the given global cycle are not touched again. This may allow an efficient execution of the proposed base method.

According to one embodiment of the method, the initial list with the defined values may be split into a plurality of sub-lists comprising sub-sequences. Furthermore, the shuffling may be performed for each sub-list separately or independently from other sub-lists. This may in particular be helpful in cases in which dependencies between hormones in the simulated gene regulatory network should be investigated. There may be cases were dependencies are already known, so that they may be treated—as part of a larger sequence of defined values—differently than others. Hence, also a random shuffling in the sub-ranges of the sequence is easily implementable.

According to one embodiment of the method, the random offset may be generated using (not being identical) a linear feedback shift register (LFSR). It may be noted that an LFSR is only one option for a random number generation generating a pseudo-random integer larger >0. Other pseudo-random integer number generators may be used instead. The LFSR random number generator may be instrumental to generate the constraint random number according to the proposed method. However, the random number generated by the LFSR is not constrained in its generated values. These may be outside the index range of the sequence.

According to another embodiment of the method, three RAM blocks with an equal number of cells may be used, wherein each RAM block may comprise the initial list with the defined values of the sequence of values to be updated. Hence, the number of RAM cells in each of the RAM blocks may be equal to the number of cells in the initial RAM block. Consequently, each RAM block may be adapted to store exactly the sequence of defined values—not less, and not more. And they may be initialized with the same sequence.

According to further embodiment of the method, shuffled output values—i.e., sequences of values—of the three RAM blocks are fed to a multiplexer. One of the output values may be selected after a fraction of a global cycle. Thus, new sequences may be made available to the simulation models time-shifted in very short amounts of time. It may be noted that the global cycle may require a plurality of local cycles and that each local cycle may need at least two machine cycles (read and write of the RAM cells) at a minimum. Of course, more than three (also two is possible) RAM blocks are possible. It may be noted that each RAM block may be controlled by its own increment counter, decrement counter, LFSR and constrained modulo value generator.

According to one additionally optional embodiment of the method, the values may be valid node indices for a gene regulatory network simulation. Thus, the proposed general concept may be instrumental for performing gene regulatory network simulations by Boolean networks requiring sequence stimuli. However, the proposed method and generator may also be used for other purposes, in which randomly generated sequences of defined values are needed.

According to one embodiment of the random sequence generator, the shuffling unit may also comprise a constraint modulo value generator using the counter and a random value generator as input values. The constraint modulo value generator may be adapted for generating the random offset value such that a sum of a counter value of the counter and the random offset values of the constraint modulo value generator is smaller or equals the number of cells in the RAM block, which equals the length of the sequence list. It may be noted that we use here the term constrained modulo value generator for generating a random offset value because it makes only sense to generate those indices that are valid addresses within the RAM block. Therefore, the randomly generated indexes have to be constrained to the limits of the total number of defined numbers within the sequence. It may be even more useful to generate only those offset values in a way that only those indexes are addressed that have not been addressed before.

According to a further embodiment of the random sequence generator, the cells of the RAM block may be dual port storage cells. This may allow for the fastest possible shuffling process.

In the following, a detailed description of the figures will be given. All instructions in the figures are schematic. Firstly, a block diagram of an embodiment of the inventive method for a random sequence generation of defined values is given. Afterwards, further embodiments, as well as embodiments of the random sequence generator for defined values, will be described.

Figure 1:
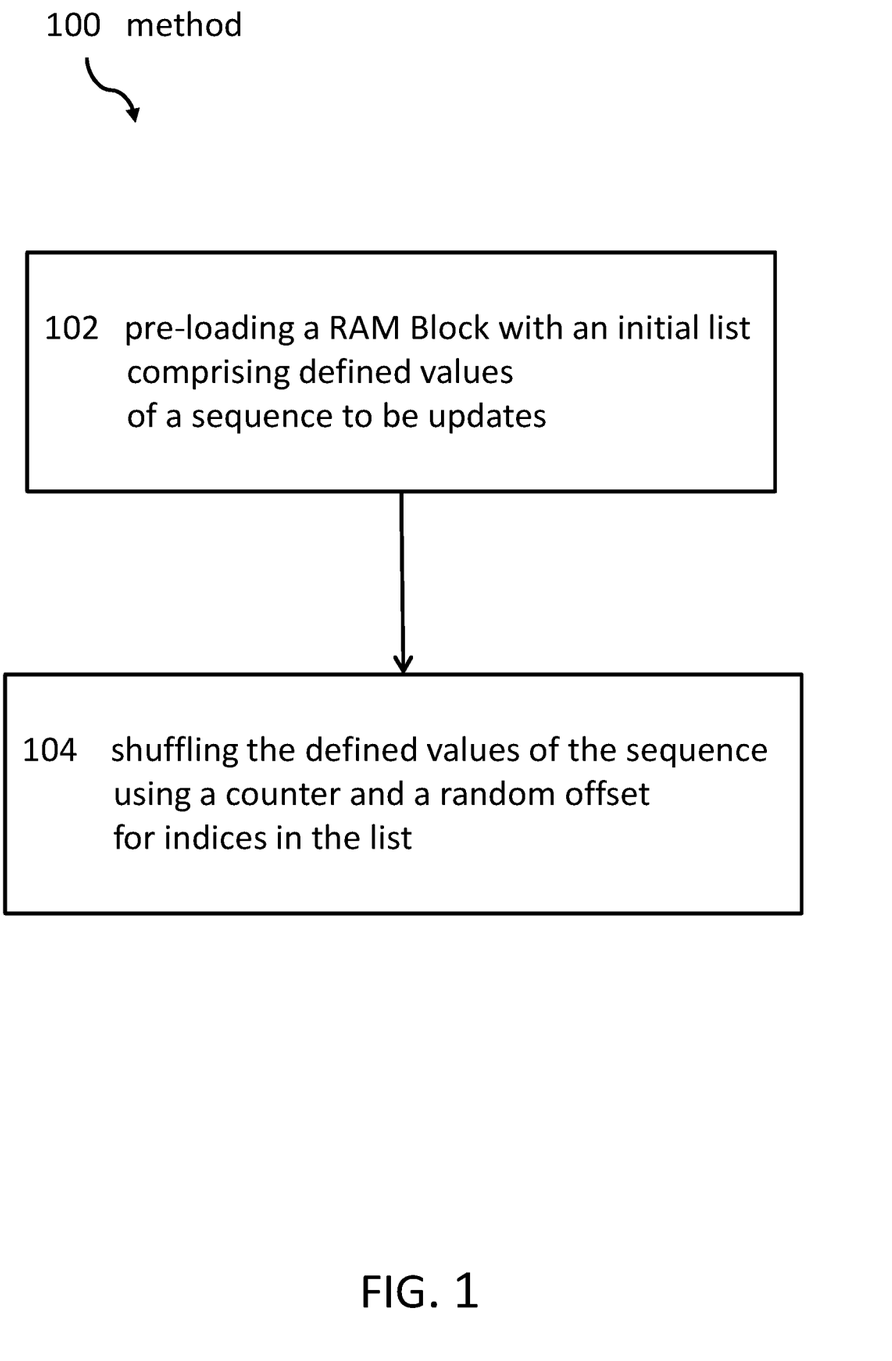
FIG. 1 shows a block diagram of an embodiment of the inventive method for a random sequence generation of defined values.

FIG. 1 shows a block diagram of an embodiment of the method 100 for a random sequence generation of defined values. The method comprises pre-loading, 102, a RAM block with an initial list comprising the defined value of a sequence of values to be updated. Hence, the RAM block is initialized with all allowed values of a sequence. Additionally, the method 100 comprises shuffling, 104, the defined values of the sequence using a counter and a random offset for indices into the list. Thus, from an initial list of values—i.e., the start sequence—a new sequence is generated comprising the same values but in a different order. In a next shuffling round, this different order is treated as initial list.

Figure 2:
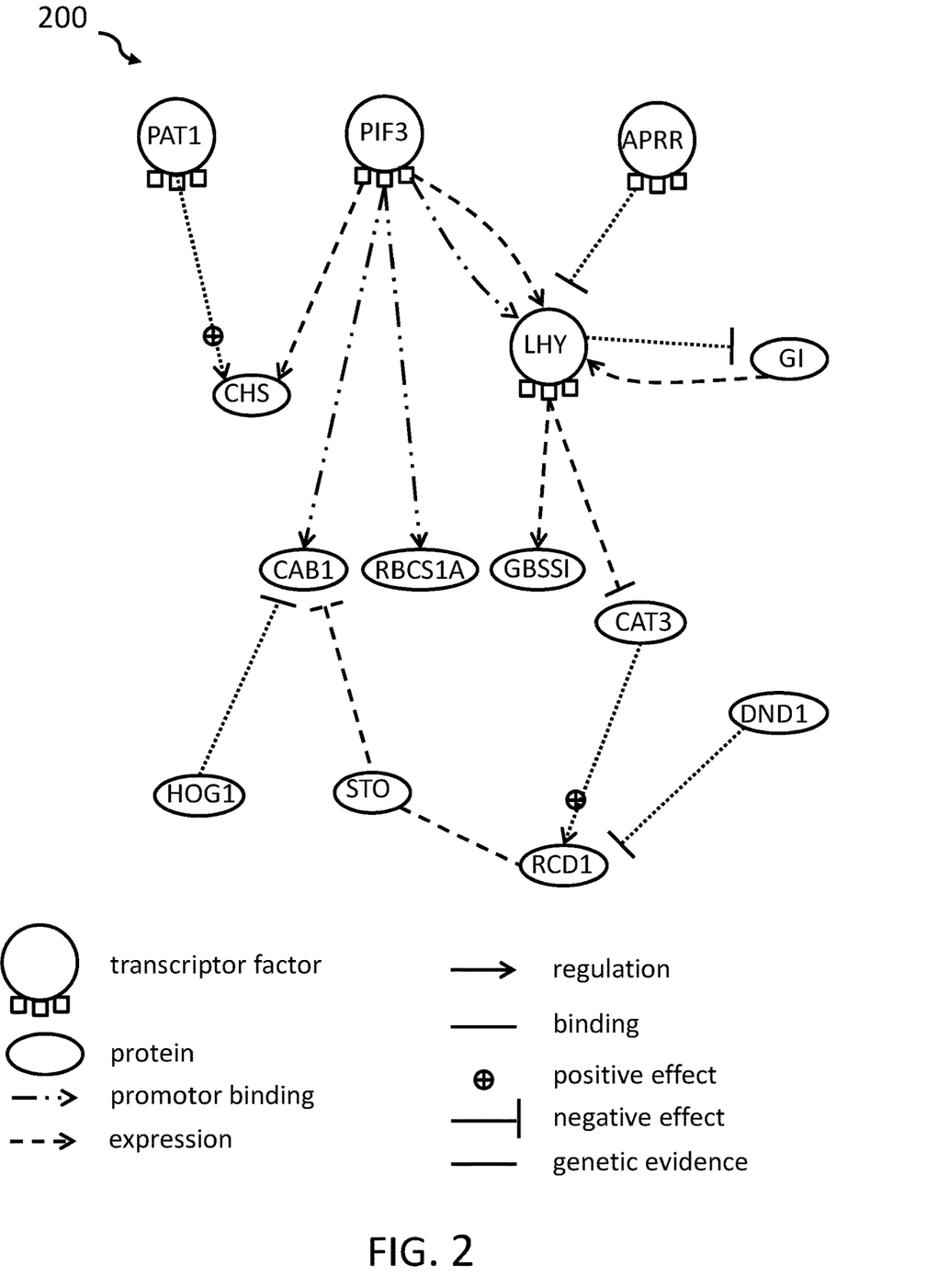
FIG. 2 shows a block diagram of a model of the gene regulatory network

FIG. 2 shows a block diagram of a model of the gene regulatory network for which the proposed method for a random number generation and the related random number generator may be used. The legend including transcription factor, protein, promotion binding, positive and negative effects as well as genetic evidence, etc., is also included in the figure. A skilled person will be able to interpret the dependencies between the different elements in the figure.

As known, genes do not work in isolation, but rather function together with other genes in complex networks. In order to achieve a more comprehensive understanding of the cellular mechanisms, interactions between genes are currently studied intensively. For this, Boolean networks (not explicitly shown) represent popular quantitative modeling techniques to simulate behaviors of biological systems. These need to be stimulated by certain patterns in order to observe how the model evolves over time. In order to study the simulated biological effects, asynchronous update schemes are used. For a better understanding of the diverse interdependencies, often only one randomly chosen gene is updated at a given time. For this, random number generators with a limited value spectrum are required, as proposed here.

Figure 3:
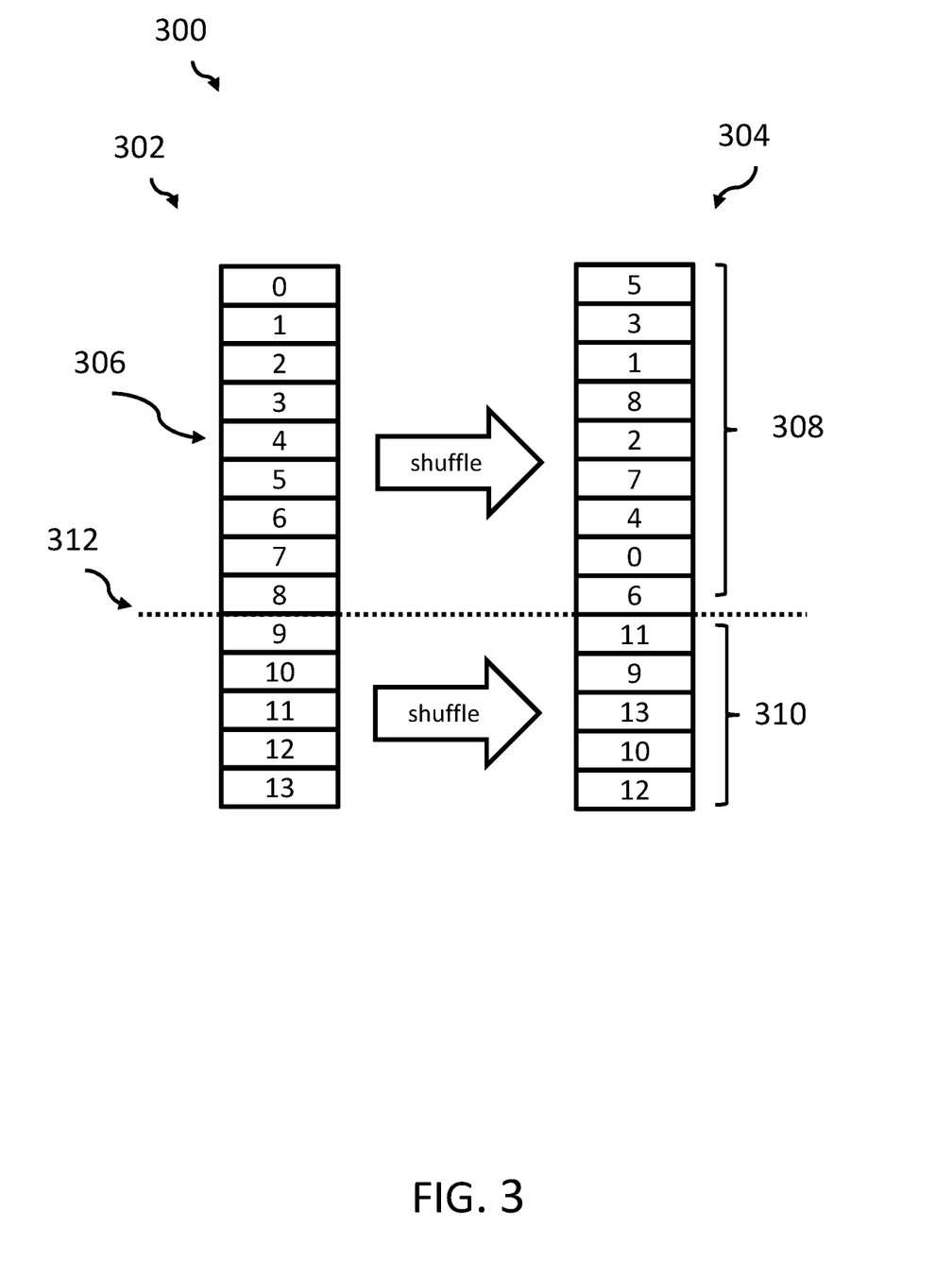
FIG. 3 shows a block diagram of a sequence of values to be preloaded in a RAM block as well as a shuffled sequence.

FIG. 3 shows a block diagram of a sequence of values to be preloaded in a RAM block 302, as well as, a shuffled sequence 304. The preloaded RAM block 302 comprises—after pre-loading—a list of defined values. In the shown example, it is an ordered list from 0 to 13. However, the values in the RAM block cells (reference sign 306 points to one of those cells as example) may have any other (integer) value. The preloaded list does not need to be sorted. It may be possible to initialize the cells 306 of the RAM block 302 with any defined number. It may also be possible—without leaving the validity of the claimed concept—that different cells 306 of the RAM block 302 may store the same value. This may be in contrast to the shown figure, in which a sorted list of unique or defined values is shown as an example.

The list or sequence 302 may be understood as one single sequence from e.g., 0 to 13, or, alternatively, the list may be split into a plurality—in this example two—sub-lists 308, 310 separated by the dashed line 312. If the sequence 302 is understood as one single list, a shuffling of the complete list may be performed resulting in the sequence 304 (it may be understood that the terms sequence and RAM blocks with cells may carry the same reference numeral 304). In case the original sequence 302 may be treated as two sub-lists 308, 310, a shuffling is only performed within the sub-lists 308, 310 separately. Typically, the length of the sequence 302, 304 may be in the range of 50 cells 306 comprising 50 values. However, a smaller number (e.g., 10) or a much higher number (e.g., 100) is possible. On the other side, there may be no upper limit because the number of hormonic influences in biological systems may be around 50,000. Thus, the sequence 302, 304 may be as long as the stimuli of the simulation model for the gene regulatory network simulation requires.

In FIG. 3, the shuffling shown is exemplary limited to the sub-lists 308 and 310. Thus, the sequence of values, 9 to 13 is only shuffled within sub-list 310. The same applies to the sub-list 308 comprising the values from 0 to 8.

Figure 4:
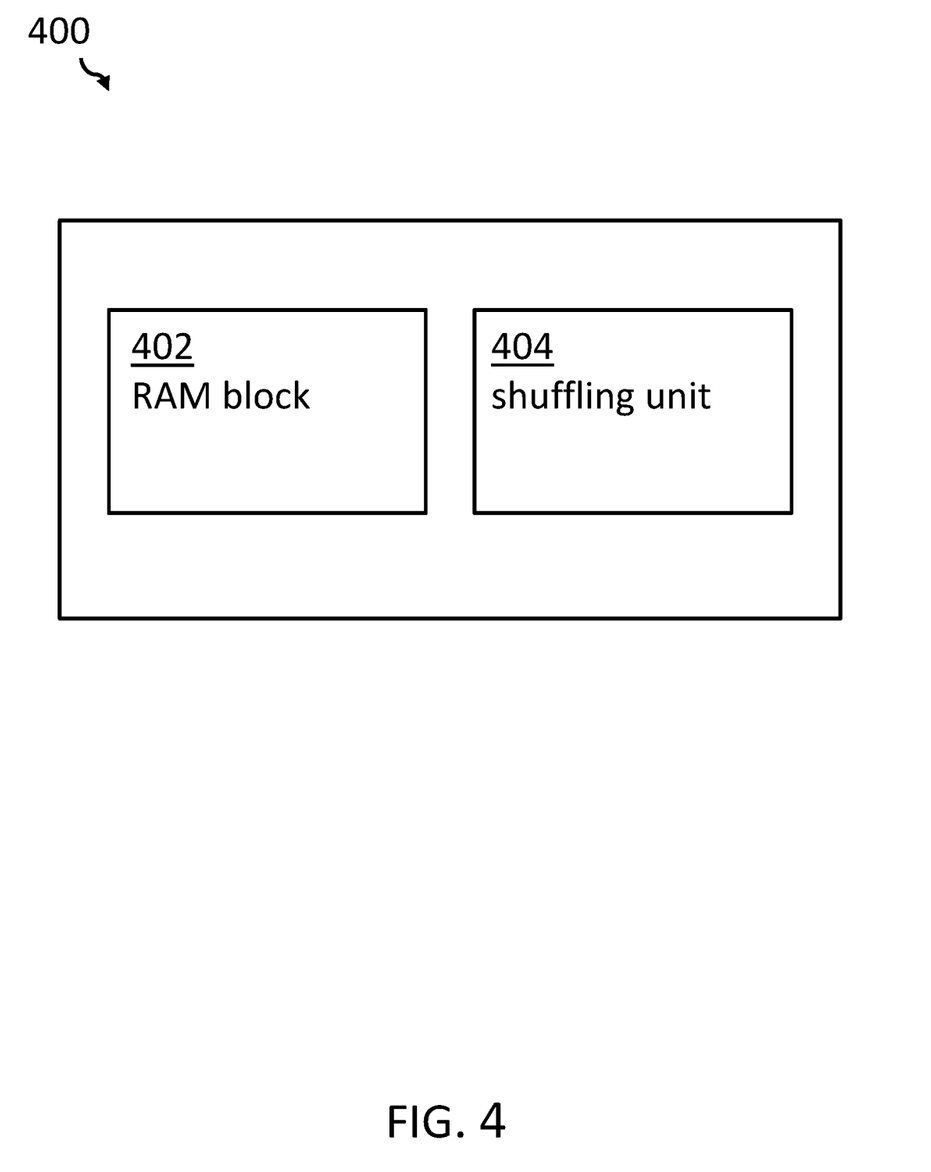
FIG. 4 shows a simplified block diagram of the random sequence generator.

FIG. 4 shows a simplified block diagram 400 of the random sequence generator. The random sequence generator comprises a RAM block 402 comprising storage cells for storing an integer value each, wherein the integer values represent an initial list with the defined values of a sequence of values to be updated, and a shuffling unit 404 adapted for shuffling the values of the sequence using a counter and a random offset for indices in the list.

Figure 5:
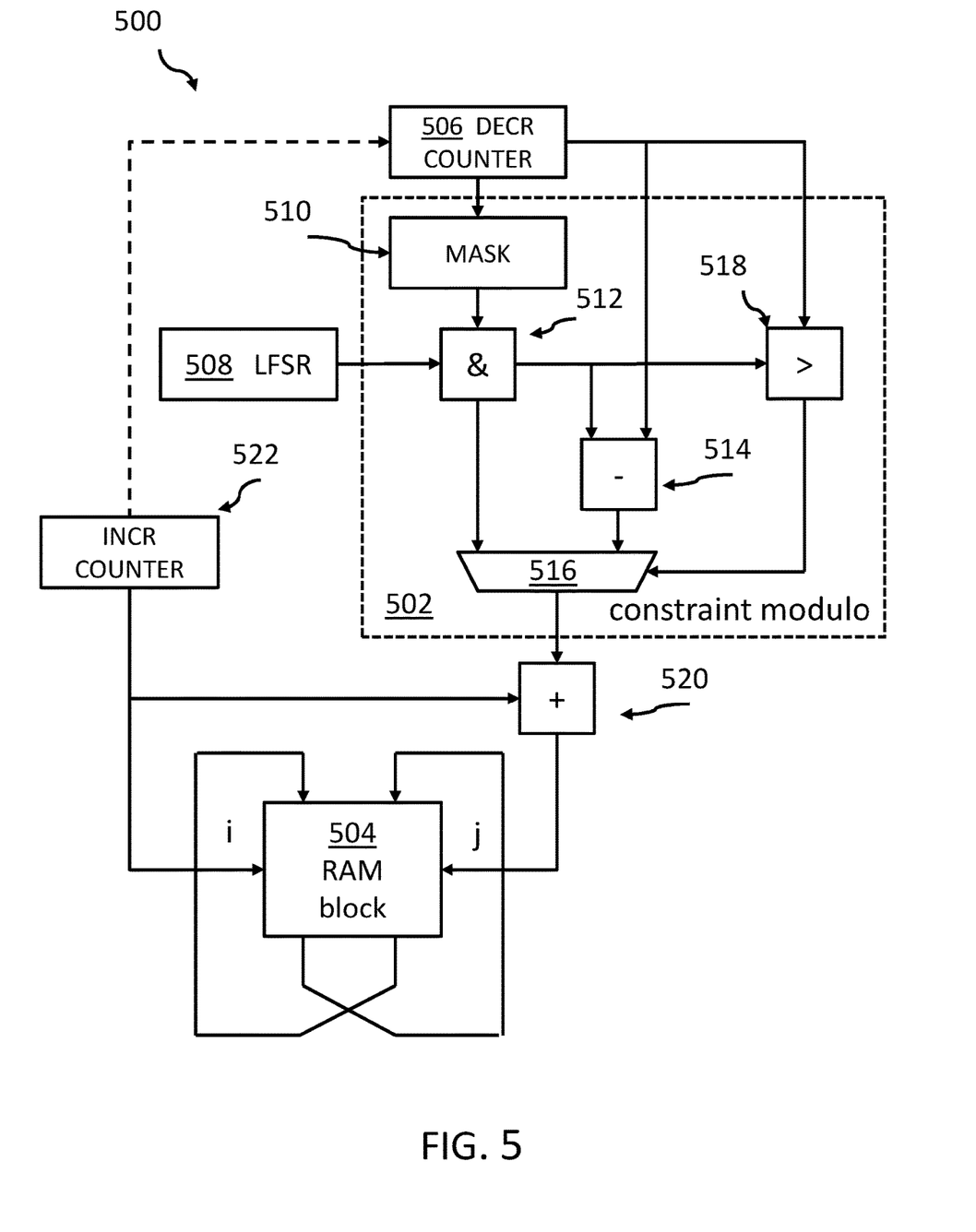
FIG. 5 shows a block diagram of a more detailed embodiment of the random sequence generator.

FIG. 5 shows a block diagram of a more detailed embodiment of the random sequence generator 500. Two main blocks comprise the constrained module value generator 502 and the RAM block 504, comprising or storing the defined values, as detailed in FIG. 3. Another acting building block is the counter 522 which runs from zero to the length of the list of defined values minus 1—i.e., it has as many counting steps as there are storage cells in the RAM block. The counter 522 is also coupled to a decrement counter 506 which goes through the index of the cells of the RAM block in a reverse order if compared to the increment counter 522. Thus, the decrement counter 506 starts with the total number of cells in the RAM block 504 minus 1 and decreases with each step down to zero. The dependency and synchronization of the two counters 522, 506 is indicated by the dashed line.

In order to better understand the function of the constrained modulo value generator 502, the shuffling process within a sequence of defined values (compare FIG. 3) should be explained using pseudo-code: A complete shuffling process—i.e., a global cycle—is executed by performing the following function:

```
for(i=0;i<n-1;i++){
  j=i+(rand( )%(n-i));
  datai   =array[i];
  dataj   =array[j];
  array[j]=datai;
  array[i]=dataj;
}
```

In each inner cycle of the for-loop (which runs from zero to n minus 1 indicated by i; n is the number of cells in the RAM block), two cells with the index i and j are shuffled/exchanged. This may represent a local cycle. After a complete run through all indices of the RAM block, i.e., the sequence, a global cycle has been finished. The function r and( ) returns a random integer value, and the % sign stands for a modulo function. Thus, the index j is determined by adding a random number to the index, wherein it is guaranteed that the index never exceeds the total number of available storage cells in the RAM block 504 (or a subtitle list). Exactly this shuffling process is performed by the elements of FIG. 5.

The index i is generated by the counter 522, whereas the index j is generated by the adding block 520, which receives as input: the value of the index i and an output of the constrained module value generator 502. These indices i and j are used to address the cells—i.e., the defined values—in the RAM block 502. In every local cycle one pair of i and j are used to exchange/shuffle the content of two cells in the RAM block 504. For this, it is useful to use dual port RAMs as the technical basis for the RAM block 502. At the bottom of the RAM block 504, values available at output ports (not explicitly shown) are fed back to input ports (not explicitly shown) of the RAM block 504. This may require machine cycles or clock cycles.

The constrained module value generator 502 works in the following way: the values of the decrement counter 506 are masked by the mask unit 510, so that only remaining cells (those which have not been shuffled yet) in the RAM block 502 are addressable. From a random number generator (e.g., LFSR), which generates a random integer number (per definition not within the limits of the allowed number of indices), an output value is forwarded to the AND function block 512, which second input value comes from the mask function 510. The output of the AND function block 512 is led to a multiplexer 516, which second input comes from a difference, building block 514, which is connected to the ADD block 512 and the current counter 506, as shown. A select signal for the multiplexer 516 comes from an output of a comparator 518, which input values come from the ADD function block 512 and the decrement counter 506, as shown in the figure.

This way, potentially each machine cycle, an index i and a corresponding index j is generated. However, only every second machine cycle such a pair of indices i, j is required because the shuffling of two cells in the RAM block 504 requires a minimum of two machine cycles. A skilled person will, without effort, understand the translation of the above shown pseudo-code into the hardware implementation.

Figure 6:
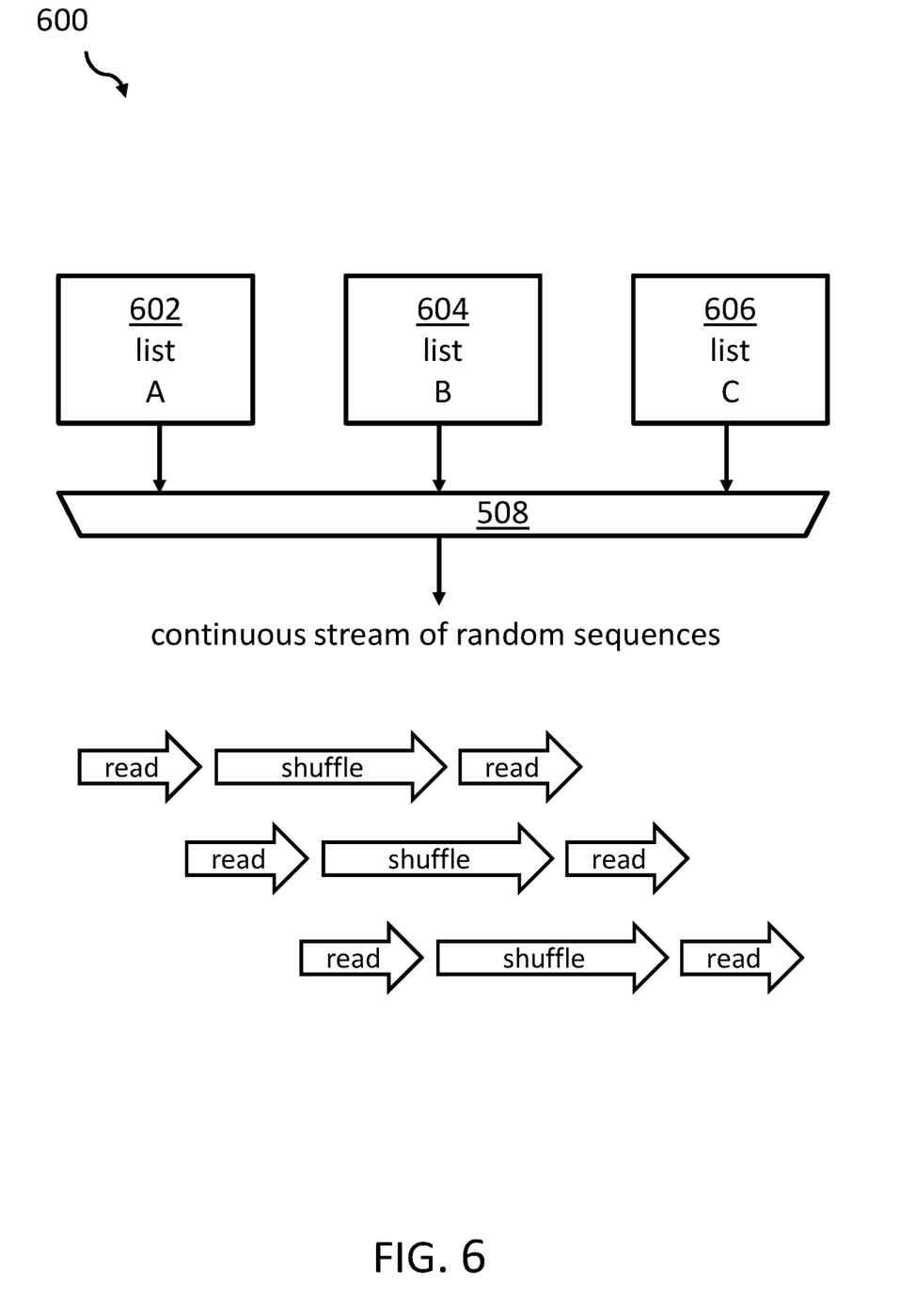
FIG. 6 shows a block diagram of three random sequence generators with related read and shuffle cycles.

FIG. 6 shows a block diagram 600 of three random sequence generators with related read and shuffle cycles. Each of the blocks 602, 604, 606 comprises at least a version of the circuit according to FIG. 5. Thus, three sequences—i.e., three lists A, B, C with defined values—are present in this embodiment. The outputs values of the 602, 604, 606 are input to a multiplexer 508 which selects—time-shifted—one of the sequence lists A, B, C at the time. This may allow a continuous flow of randomly generated sequences to be used in the gene regulatory network simulation—i.e., as input values for the simulating Boolean network. Because the circuit according to FIG. 5 requires two machine cycles to shuffle the content of two cells of the RAM block 544 only a limited number of random sequences may become available for the simulation process. Thus, by letting run a plurality (in this example, three) of sequence shuffling processes, a continuous flow of randomly generated sequences of defined values may be generated in a time-shifted manner. It should be understood that more than three of the circuits according to FIG. 5 may be operable in parallel in order to increase the generated number of sequences per time unit.

The lower part of FIG. 6 illustrates the overlap between the read and shuffle processes of the different functional blocks 602, 604, 606. Each of the arrow lines may correspond to one of the functional blocks 602, 604, 606. Because the shuffling requires a certain amount of time, a parallel, but timewise displaced functional block starts with the generation of a new random sequence somewhere in the middle of the execution of first mentioned functional block, and so on. This way, the number of randomly generated sequences per time unit can be increased, elegantly.

Figure 7:
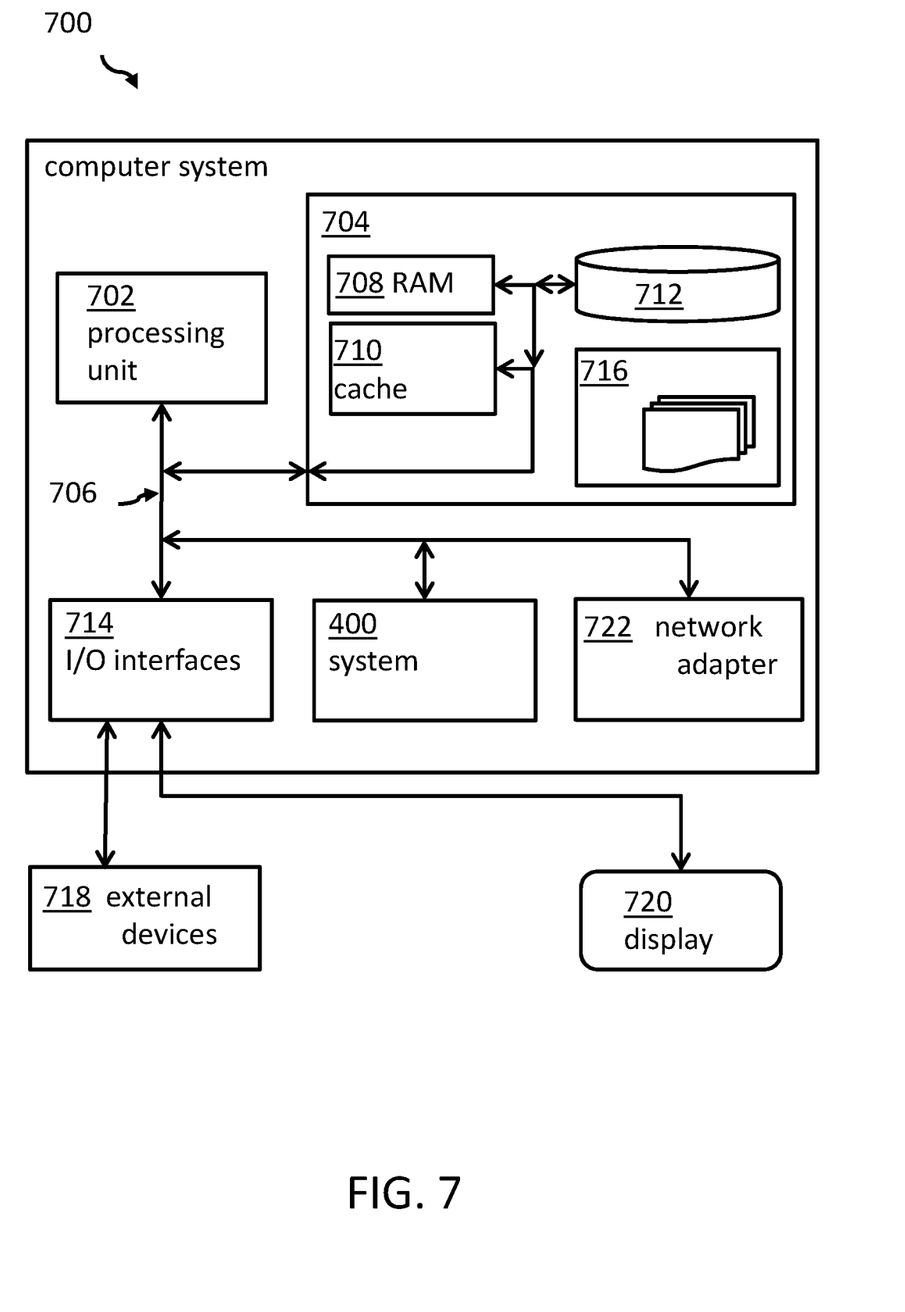
FIG. 7 shows a block diagram of a computing system instrumental for executing the proposed method.

Embodiments of the invention may be implemented together with virtually any type of computer, regardless of the platform being suitable for storing and/or executing program code. FIG. 7 shows, as an example, a computing system 700 suitable for executing program code related to the proposed method.

The computing system 700 is only one example of a suitable computer system and is not intended to suggest any limitation as to the scope of use or functionality of embodiments of the invention described herein, regardless, whether the computer system 700 is capable of being implemented and/or performing any of the functionality set forth hereinabove. In the computer system 700, there are components, which are operational with numerous other general purpose or special purpose computing system environments or configurations. Examples of well-known computing systems, environments, and/or configurations that may be suitable for use with computer system/server 700 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like. Computer system/server 700 may be described in the general context of computer system-executable instructions, such as program modules, being executed by a computer system 700. Generally, program modules may include routines, programs, objects, components, logic, data structures, and so on that perform particular tasks or implement particular abstract data types. Computer system/server 700 may be practiced in distributed cloud computing environments where tasks are performed by remote processing devices that are linked through a communications network. In a distributed cloud computing environment, program modules may be located in both, local and remote computer system storage media including memory storage devices.

As shown in the figure, computer system/server 700 is shown in the form of a general-purpose computing device. The components of computer system/server 700 may include, but are not limited to, one or more processors or processing units 702, a system memory 704, and a bus 706 that couple various system components including system memory 704 to the processor 702. Bus 706 represents one or more of any of several types of bus structures, including a memory bus or memory controller, a peripheral bus, an accelerated graphics port, and a processor or local bus using any of a variety of bus architectures. By way of example, and not limiting, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus. Computer system/server 700 typically includes a variety of computer system readable media. Such media may be any available media that is accessible by computer system/server 700, and it includes both, volatile and non-volatile media, removable and non-removable media.

The system memory 704 may include computer system readable media in the form of volatile memory, such as random access memory (RAM) 708 and/or cache memory 710. Computer system/server 700 may further include other removable/non-removable, volatile/non-volatile computer system storage media. By way of example only, a storage system 712 may be provided for reading from and writing to a non-removable, non-volatile magnetic media (not shown and typically called a 'hard drive'). Although not shown, a magnetic disk drive for reading from and writing to a removable, non-volatile magnetic disk (e.g., a 'floppy disk'), and an optical disk drive for reading from or writing to a removable, non-volatile optical disk such as a CD-ROM, DVD-ROM or other optical media may be provided. In such instances, each can be connected to bus 706 by one or more data media interfaces. As will be further depicted and described below, memory 704 may include at least one program product having a set (e.g., at least one) of program modules that are configured to carry out the functions of embodiments of the invention.

The program/utility, having a set (at least one) of program modules 716, may be stored in memory 704 by way of example, and not limiting, as well as an operating system, one or more application programs, other program modules, and program data. Each of the operating systems, one or more application programs, other program modules, and program data or some combination thereof, may include an implementation of a networking environment. Program modules 716 generally carry out the functions and/or methodologies of embodiments of the invention, as described herein.

The computer system/server 700 may also communicate with one or more external devices 718 such as a keyboard, a pointing device, a display 720, etc.; one or more devices that enable a user to interact with computer system/server 700; and/or any devices (e.g., network card, modem, etc.) that enable computer system/server 700 to communicate with one or more other computing devices. Such communication can occur via Input/Output (I/O) interfaces 714.

Still yet, computer system/server 700 may communicate with one or more networks such as a local area network (LAN), a general wide area network (WAN), and/or a public network (e.g., the Internet) via network adapter 722. As depicted, network adapter 722 may communicate with the other components of computer system/server 700 via bus 706. It should be understood that although not shown, other hardware and/or software components could be used in conjunction with computer system/server 700. Examples, include, but are not limited to: microcode, device drivers, redundant processing units, external disk drive arrays, RAID systems, tape drives, and data archival storage systems, etc.

Additionally, random sequence generator for defined 400 may be attached to the bus system 706.

The descriptions of the various embodiments of the present invention have been presented for purposes of illustration, but are not intended to be exhaustive or limited to the embodiments disclosed. Many modifications and variations will be apparent to those of ordinary skills in the art without departing from the scope and spirit of the described embodiments. The terminology used herein was chosen to best explain the principles of the embodiments, the practical application or technical improvement over technologies found in the marketplace, or to enable others of ordinary skills in the art to understand the embodiments disclosed herein.

The present invention may be embodied as a system, a method, and/or a computer program product. The computer program product may include a computer readable storage medium (or media) having computer readable program instructions thereon for causing a processor to carry out aspects of the present invention.

The medium may be an electronic, magnetic, optical, electromagnetic, infrared or a semi-conductor system for a propagation medium. Examples of a computer-readable medium may include a semi-conductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), DVD and Blu-Ray-Disk.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object-oriented programming language such as Smalltalk, C++ or the like, and conventional procedural programming languages, such as the "C" programming language or similar programming languages. The computer readable program instructions may execute entirely on the user's computer, partly on the user's computer as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus', and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus', or another devices to cause a series of operational steps to be performed on the computer, other programmable apparatus or other device to produce a computer implemented process, such that the instructions which execute on the computer, other programmable apparatus', or another device implement the functions/acts specified in the flowchart and/or block diagram block or blocks.

The flowcharts and/or block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or act or carry out combinations of special purpose hardware and computer instructions.

The terminology used herein is for the purpose of describing particular embodiments only and is not intended to limit the invention. As used herein, the singular forms "a", "an" and "the" are intended to include the plural forms as well, unless the context clearly indicates otherwise. It will further be understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or steps plus function elements in the claims below are intended to include any structure, material, or act for performing the function in combination with other claimed elements, as specifically claimed. The description of the present invention has been presented for purposes of illustration and description, but is not intended to be exhaustive or limited to the invention in the form disclosed. Many modifications and variations will be apparent to those of ordinary skills in the art without departing from the scope and spirit of the invention. The embodiments are chosen and described in order to best explain the principles of the invention and the practical application, and to enable others of ordinary skills in the art to understand the invention for various embodiments with various modifications, as are suited to the particular use contemplated.

What is claimed is:

1. A method of a random sequence generation of defined values, the method comprising
    pre-loading a RAM block with an initial list comprising the defined values of a sequence of values to be updated, and
    shuffling the defined values of the sequence using a counter and a random offset for indices in the list, wherein the initial list with the defined values is split into a plurality of sub-lists comprising sub-sequences, and wherein the shuffling is performed for each sub-list, wherein the random sequence generation is used to generate a plurality of stimuli for a gene regulatory network simulation and wherein a usage of hardware resources for the gene regulatory network simulation is optimized by minimizing the hardware resources from being in wait states waiting for a next randomly generated sequence of defined values.

2. The method according to claim 1, wherein the shuffling exchanges two defined values in each local cycle.

3. The method according to claim 2, wherein a global cycle of the shuffling is completed after the counter has run through all values from the start value to the end value resulting in a new sequence of the defined values.

4. The method according to claim 2, wherein in a local cycle only those values of the sequence are exchanged that have not been shuffled in a previous local cycle.

5. The method according to claim 1, wherein a start value of the counter is zero and an end value of the counter is equal to a length value of the list minus 1, and wherein each counter increase represents one local cycle.

6. The method according to claim 1, wherein the random offset is generated using a linear feedback shift register.

7. The method according to claim 1, wherein three RAM blocks with an equal number of cells are used, each RAM block comprising the initial list with the defined values of the sequence of values to be updated.

8. The method according to claim 7, wherein shuffled output values of the three RAM blocks are fed to a multiplexer, and wherein one of the output values is selected after a fraction of a local cycle.

9. The method according to claim 1, wherein the defined values are valid node indices for a gene regulatory network simulation.

10. A random sequence generator for defined values, the random sequence generator comprising:
a RAM block comprising storage cells for storing an integer value each, wherein the integer values represent an initial list with the defined values of a sequence of values to be updated; and
a shuffling unit adapted for shuffling the values of the sequence using a counter and a random offset for indices in the list,
wherein the shuffling unit comprises a constraint modulo value generator using the counter and a random number generator, wherein the constraint modulo value generator is adapted for generating random offset values such that a sum of a counter value of the counter and the random offset values, of the constraint modulo value generator is smaller or equal the number of cells in the RAM block,
wherein the random sequence generation is used to generate a plurality of stimuli for a gene regulatory network simulation and wherein a usage of hardware resources for the gene regulatory network simulation is optimized by minimizing the hardware resources from being in wait states waiting for a next randomly generated sequence of defined values.

11. The random sequence generator according to claim 10, wherein the shuffling unit is adapted for exchanging two defined values in the RAM block in each local cycle.

12. The random sequence generator according to claim 10, wherein a start value of the counter is zero and an end value of the counter is equal to a length value of the list minus 1, and wherein each counter increase represents one local cycle.

13. The random sequence generator according to claim 12, wherein a global cycle of the shuffling is completed after the counter has run through all values from the start value to the end value resulting in a new sequence of the defined values.

14. The random sequence generator according to claim 12, wherein in a local cycle only those values of the sequence are exchanged that have not been shuffled in a previous cycle of a global cycle.

15. The random sequence generator according to claim 10, wherein the RAM block is split into a plurality of sub-RAM blocks comprising sub-sequences, and wherein the shuffling unit is adapted for performing the shuffling for each sub-RAM block.

16. The random sequence generator according to claim 10, wherein the cells of the RAM block are dual port storage cells.

17. The random sequence generator according to claim 10, comprising also two additional RAM blocks, each with as many storage cells as the RAM block, each of the RAM blocks preloaded with the initial list with the defined values of a sequence of values to be updated, and
a multiplexer adapted for selecting shuffled output values of one of the three RAM blocks, wherein one of the output values is selected after a fraction of a local cycle.

18. A computer program product for a random sequence generation of defined values, said computer program product comprising a computer readable storage medium having program instructions embodied therewith, said program instructions being executable by one or more computing systems to cause said one or more computing systems to
pre-load a RAM block with an initial list comprising the defined values of a sequence of values to be updated, and
shuffle the defined values of the sequence using a counter and a random offset for indices in the list,
wherein the initial list with the defined values is split into a plurality of sub-lists comprising sub-sequences, and wherein the shuffling is performed for each sub-list,
wherein the random sequence generation is used to generate a plurality of stimuli for a gene regulatory network simulation and wherein a usage of hardware resources for the gene regulatory network simulation is optimized by minimizing the hardware resources from being in wait states waiting for a next randomly generated sequence of defined values.

* * * * *